United States Patent [19]

Partenheimer et al.

[11] Patent Number: 4,786,753
[45] Date of Patent: Nov. 22, 1988

[54] OXIDATION PROCESS FOR THE MANUFACTURE OF AROMATIC ACIDS FROM ALKYLAROMATIC COMPOUNDS

[75] Inventors: Walter Partenheimer; Wayne P. Schammel, both of Naperville, Ill.

[73] Assignee: Amoco Corporation, Chicago, Ill.

[21] Appl. No.: 50,860

[22] Filed: May 18, 1987

[51] Int. Cl.$^4$ .......................................... C07C 51/265
[52] U.S. Cl. ................................. 562/416; 502/102; 502/169; 562/412; 562/417; 562/480
[58] Field of Search ............... 562/412, 416, 417, 480; 502/102, 169

[56] References Cited

U.S. PATENT DOCUMENTS

| | | | |
|---|---|---|---|
| 2,245,528 | 6/1941 | Loder | 562/417 |
| 2,833,816 | 5/1958 | Saffer et al. | 562/416 |
| 3,155,718 | 11/1964 | Brown et al. | 562/416 |
| 3,819,695 | 6/1974 | Yamashita et al. | 562/416 |

FOREIGN PATENT DOCUMENTS 0041784 12/1981 European Pat. Off. .
0010229 1/1977 Japan .

Primary Examiner—Werren B. Lone
Assistant Examiner—Vera C. Clarke
Attorney, Agent, or Firm—Gunar J. Blumberg; William H. Magidson; Ralph C. Medhurst

[57] ABSTRACT

A novel method of oxidizing di- and trimethylbenzenes with molecular oxygen to the corresponding di- or tricarboxylic acid under liquid-phase conditions is disclosed. The process is conducted at a temperature of about 100° C. to 260° C. This process comprises conducting the oxidation in the presence of a catalyst system comprising a source of bromine with nickel, manganese and zirconium. The benzene di- and tricarboxylic acids have wide industrial application, including the manufacture of polyesters, polyamides, and fibers and films.

6 Claims, No Drawings

OXIDATION PROCESS FOR THE MANUFACTURE OF AROMATIC ACIDS FROM ALKYLAROMATIC COMPOUNDS

FIELD OF THE INVENTION

Addition of nickel and zirconium to oxidation catalysis provided by heavy, transition metal-bromine ion combination containing at least manganese ion uniquely increases catalytic activity of said combination for converting methyl groups to carboxylic acid groups on benzene nucleus and enables the elimination of the expensive catalyst, cobalt. Such greater catalytic activity is manifested by longer sustained initial rapid rate of oxygen consumption, lower solvent burning and improved yield.

BACKGROUND OF THE INVENTION

The possibility of using liquid-phase instead of vapor-phase oxidation for the preparation of benzene carboxylic acids was first indicated by the disclosure in U.S. Pat. No. 2,245,528 of the catalysis provided by transition of variable valence metals, especially cobalt, in a liquid phase of saturated lower aliphatic acid at temperatures from about 100° C. to about 320° C. and pressures to maintain the liquid phase of the aliphatic acid. Such catalysis, according to said patent, was advantageously promoted by the use of a ketone such as methylethyl ketone or aldehyde such as acetaldehyde. Unfortunately such aldehyde or ketone promoted variable valence metal catalysis was useful only for converting mono-, di- and tri-methylbenzenes to their respective benzene monocarboxylic acids: benzoic, toluic and dimethyl benzoic acids. Two separate, later and somewhat parallel lower temperature (80° C.-100° C.) modifications of the aldehyde or ketone promoted cobalt catalysis in liquid phase of acetic acid did provide commercially feasible conversion of xylenes to phthalic acids, especially p-xylene to terephthalic acid but only at the expense of using rather high concentrations of cobalt. Combinations of cobalt and manganese with a source of bromine became preferred for commercial use and are disclosed in U.S. Pat. No. 2,833,816. However, cobalt is very expensive and also available only from sources outside the United States and from countries which may cut off the supply of this valuable metal.

For liquid-phase oxidation of dimethylbenzenes or pseudocumene with molecular oxygen it has been discovered that nickel and zirconium are unique among metals for substantially enhancing the activity of the bromine-manganese systems of catalysis.

It is surprising that nickel and zirconium are effective in combination with manganese. In our process it is critical that bromine be present. Good yields are not obtained if bromine is not present. Japanese Kokai No. 77 10,229, German Offenlegungsschrift No. 2,804,156, U.S. Pat. No. 2,833,816 and European patent application No. 0,041,784 disclose nickel catalysts, but not in combination with manganese or zirconium.

The world capacity exceeds ten billion pounds of terephthalic acid. Presently, purified terephthalic acid is produced in two stages, (1) oxidation of paraxylene using dioxygen, a cobalt/manganese/bromine catalyst in an acetic acid solvent, and (2) purifying the crude TA cake by recrystallizing and hydrogenating it in water. Cobalt is the most expensive component of the catalyst system. Therefore, there is great economic incentive to replace cobalt with some other metal. Our novel process has succeeded in doing just this.

For the present invention the gram-atom ratio of nickel-zirconium-manganese is in the range of about 33:1:12 to about 80:1:43. The preferred range is about 40:1:20 to about 70:1:40. The ratio of total metals, Ni plus manganese plus zirconium to bromine is in the range of about 0.5 to about 1.5 on the milligram atom basis. Thus for each gram-mole of p-xylene, m-xylene, or pseudocumene in the oxidation there is used from about 4 to about 20 milligram atom nickel, about 0.10 to about 0.30 milligram atom zirconium, about 2 to about 10 total of Mn and from about 8 to about 24 milligram atoms bromine. The preferred metal to bromine ratio for pseudocumene is about 0.7 to about 1.0 and for metaxylene it is about 0.7 to about 1.0 and for paraxylene it is about 0.7 to about 1.0. The nickel-zirconium catalyst is also useful in oxidation system process, where water was replaced with aliphatic acids containing less than five carbon atoms, such as acetic acid as the reaction medium.

Nickel and zirconium can be added to the reaction in any form soluble in the di- or trimethylbenzene being oxidized in acetic acid. For example, nickel or zirconium octanoate or naphthanate can be used with manganese octanoates or naphthenics for oxidation of the di- or trimethylbenzenes in the absence of reaction solvent and Ni, Zr and Mn can be conveniently used as their acetates when di- or trimethylbenzenes are oxidized in the presence of acetic acid solvent. Nickel and zirconium are readily available and are ideally suited for liquid-phase oxidations using acetic acid or water as reaction solvent.

The source of molecular oxygen for the nickel and zirconium enhanced oxidation of this invention can vary in $O_2$ content from that of air to oxygen gas. Air was the preferred source of molecular oxygen for oxidations conducted at temperatures at 100° C. and above up to 260° C. For oxidations conducted with molecular oxygen the preferred temperatures were in the range of about 120° C. to about 220° C. The minimum pressure for such oxidations was that pressure which will maintain a substantial liquid phase 70-80%, of the reaction medium either neat di- or trimethylbenzene or such methylbenzene and 70-80% of the acetic acid. The acetic acid or water solvent, when used, can amount to 1-10 parts on weight basis per part of the di- or trimethylbenzene. The methylbenzene and/or acetic acid not in the liquid phase because of vaporization by heat of reaction was advantageously condensed and the condensate returned to the oxidation as a known means for removing heat and thereby temperature controlling the exothermic oxidation reaction.

The benefits to be derived from the use of nickel and zirconium according to the present invention were indicated by results shown with respect to the following illustrative and comparative oxidations using pseudocumene, m-xylene or p-xylene as the methyl-substituted benzene to be oxidized.

The batchwise oxidations were conducted by charging all of the catalyst components, pseudocumene, p-xylene or m-xylene and acetic acid or water, sealing the reactor; setting a pressure control valve initially to 150 psig (valve was in exhaust vent line); pressuring the reactor to 150 psig with nitrogen; heating the reactor contents to the desired temperature, 160° C. for pseudocumene, and then introducing pressurized air into the liquid phase in the reactor at a constant flow rate. Cooling water at approximately 20° C. was introduced into the jacket of the condenser section. Each oxidation was terminated as close to 14 percent vent oxygen by volume as was feasible to do.

In the examples to follow all oxidations were conducted initially at a gauge pressure of 150 pounds per square inch (psig) and at oxidation initiation temperature of 160° C. for pseudocumene, using a weight ratio of acetic acid to pseudocumene or xylene of about 1.87:1 and using air as the source of molecular oxygen. The oxidation reactor used was a stirred 2-liter titanium cylindrical autoclave. A water-cooled condensor was placed immediately above the autoclave to condense and return a substantial portion of the volatile compound. Following the condensation system, there were means for venting the exhaust gaseous mixture (nitrogen, unused or excess oxygen, oxides of carbon, water vapor, and vapor of uncondensed acetic acid and some of the unreacted xylene) and analytical means for determining the oxygen, carbon dioxide, and carbon monoxide contents of exhaust sample on acetic acid-free dry basis. The exhaust sample flowed through three cooled (e.g. dry ice-acetone cooled) traps before analysis for $O_2$, $CO_2$ and CO. The reactor was charged with 225 grams of pseudocumene or xylene, thus 420 grams acetic acid for the 1.87:1 solvent to pseudocumene weight ratio. The oxidation of pseudocumene was conducted batchwise by charging all of the catalyst components, pseudocumene and acetic acid, to the reactor. The reactor was sealed. The pressure control valve was set initially at 150 psig (valve was in exhaust vent line). The pressure was gradually increased from 150 psig to 400 psig for 55 minutes. Accordingly the temperature increased from 160° C. to 210° C. in the same time period. The reactor was pressured to 150 psig with nitrogen and then heated to the initiation temperature. Thereafter pressurized air was introduced into the liquid phase in the reactor. Each oxidation was terminated as close to 14% vent oxygen by volume as was feasible to do.

After termination of the oxidations, the total reactor effluents (hereafter "TRE") was collected. The resulting TRE products were submitted for aromatic acid analysis.

Product yield were calculated (and hereafter reported) in mole percent of product per mole pseudocumene or xylene charged.

Other pertinent details of the illustrative oxidations and the results so produced are presented hereafter in Tables I and II. Nickel and zirconium were used as nickel and zirconium acetate but other acetic acid or water soluble nickel and zirconium compounds are suitable for my novel process. Manganese was used as its own acetate tetrahydrates. The source of bromine was hydrobromic acid but other bromine sources, e.g., HBr, $BR_2$, KBr, Nabr, $NH_4Br$, benzyl bromide, tetrabromoethane, etc., are useful.

EXAMPLES

The Ni/Br, Mn/Br, and Mn/Zr/Br catalyst combinations were active in the oxidation of alkylaromatic oxidations as shown in examples 2, 4, 8 on Table I. A synergistic interaction is defined as the action of discrete agencies in which the total effect is greater than the sum of their effects when acting independently. For example, if the effect is defined as the rate of oxidation of pseudocumene (as determined in a mini-reactor run at 100° C.), then if the sum of rates of a Ni/Br and a Mn/Zr/Br catalyst is less than a Ni/Mn/Zr/Br catalyst, a synergistic interaction has occurred. In homogeneous oxidations increased catalyst concentrations normally result in increased rates of oxidation, as shown in examples 1, 2 and 3, 4 and 6, 7 and 8, 9 on Table I. It is therefore important when determining if a synergistic interaction has occurred, to be sure that equal catalyst concentrations are being compared. In the following examples this proviso has been observed. All examples are rates of oxidation, in ml $O_2$/min from Table I.

In this specification fifteen examples illustrate the synergism of the Ni/Mn/Zr/Br catalytic system.

The product of all alkylaromatic oxidations to aromatic acids was water. The concentration of the water in the acetic acid varied depending on the number of alkyl groups on the aromatic compound, the pressure of the oxidation, etc. Therefore, the rates of oxidation were measured as a function of water in the mini-reactors on Table I. It was apparent that the synergistic interaction exists at all water concentrations in acetic acid.

Comparison of examples 12 and 13 to 14 on Table I illustrates that Ni/Mn/Zr/Br catalysts had the same activity as that expected from cobalt/manganese/bromine catalyst.

The catalyst variable which had the greatest effect on the yield was the nickel concentration.

In Table I the experimental data is set forth where pseudocumene was the oxidant while in Table II paraxylene and metaxylene were the oxidants. The synergistic effect of zirconium on Ni/Mn/Br catalyst was observed with all of these feedstocks.

TABLE I

Rate of Oxidation of Various Types of Catalysts[a]
In the Oxidation of Pseudocumene to Trimellitic Acid

| Example | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Type of Catalyst | Ni/Br | Ni/Br | Mn/Br | Mn/Br | Zr/Br | Ni/Zr/Br | Ni/Zr/Br | Mn/Zr/Br | Mn/Zr/Br | Ni/Mn/Br | Ni/Mn/Br | Ni/Mn/Zr/Br | Ni/Mn/Zr/Br | Co/Mn/Br |
| Catalyst, mmol | | | | | | | | | | | | | | |
| Nickel | 2.01 | 4.02 | 0.0 | 0.0 | 0.0 | 2.02 | 4.02 | 0.0 | 0.0 | 2.01 | 2.01 | 2.01 | 2.01 | 2.01 |
| Manganese | 0.0 | 0.0 | 2.01 | 4.02 | 0.0 | 0.0 | 0.0 | 2.01 | 4.02 | 2.01 | 2.01 | 2.01 | 2.01 | 2.01 |
| Zirconium | 0.0 | 0.0 | 0.0 | 0.0 | 0.19 | 0.19 | 0.38 | 0.19 | 0.38 | 0.0 | 0.0 | 0.38 | 0.38 | 0.0 |
| Bromide | 2.01 | 4.02 | 2.01 | 4.02 | 0.19 | 2.02 | 4.02 | 2.01 | 4.02 | 4.02 | 4.02 | 4.02 | 4.02 | 4.02 |
| Oxidation Rate, ml $O_2$/min | | | | | | | | | | | | | | |
| at 0.3% $H_2O$ | 0.0 | 0.05 | 1.18 | 1.26 | 0.0 | 0.0 | 0.05 | 2.21 | 5.91 | 6.78 | 6.53 | 7.01 | 6.06 | 5.64 |
| at 5.0% $H_2O$ | 0.0 | — | 1.87 | .58 | 0.0 | 0.0 | — | 2.30 | 4.80 | 2.46 | 1.78 | 5.60 | 5.30 | 4.33 |
| at 13.0% $H_2O$ | 0.0 | — | 0.71 | .10 | 0.0 | 0.0 | — | 1.32 | 3.71 | 0.51 | 0.46 | 3.00 | 4.22 | 1.43 |

TABLE I-continued

Rate of Oxidation of Various Types of Catalysts[a]
In the Oxidation of Pseudocumene to Trimellitic Acid

| | Example | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| | | | | | | | | Type of Catalyst | | | | | | |
| | Ni/Br | Ni/Br | Mn/Br | Mn/Br | Zr/Br | Ni/Zr/Br | Ni/Zr/Br | Mn/Zr/Br | Mn/Zr/Br | Ni/Mn/Br | Ni/Mn/Br | Ni/Mn/Zr/Br | Ni/Mn/Zr/Br | Co/Mn/Br |
| at 20.0% $H_2O$ | 0.0 | — | 0.05 | .05 | 0.0 | 0.0 | | 0.46 | 1.44 | 0.10 | 0.15 | 1.16 | 1.29 | 0.77 |

[a]Reactions were run in a glass reactor containing 10.0 ml pseudocumene and 100.0 ml acetic acid. The source of oxygen was air which was passed through a glass frit at the bottom of the reactor at a rate of 52 ml/min. The vent oxygen concentration was constantly measured using a Beckman oxygen analyzer. The rate of oxygen uptake was calculated from the vent oxygen concentration and the flow rate of air through the reactor. The temperature was maintained at 95° C. and the pressure was atmospheric.

TABLE II

Rate of Oxidation of Various Types of Catalysts[a]
For the Oxidation of Paraxylene or Metaxylene

| | Example | | | |
|---|---|---|---|---|
| | 15 | 16 | 17 | 18 |
| | Type of Catalyst | | | |
| | Ni/Mn/Br | Ni/Mn/Zr/Br | Ni/Mn/Br | Ni/Mn/Zr/Br |
| Catalyst, mmol | | | | |
| Nickel | 2.01 | 2.01 | 2.01 | 2.01 |
| Manganese | 2.01 | 2.01 | 2.01 | 2.01 |
| Zirconium | 0.0 | .19 | 0.0 | 0.19 |
| Bromide | 4.02 | 4.02 | 2.01 | 4.02 |
| Oxidation Rate, ml $O_2$/min | | | | |
| at 0.3% $H_2O$ | 2.92 | 5.70 | 6.68 | 6.31 |
| at 5.0% $H_2O$ | 0.49 | 2.13 | .56 | 1.66 |
| at 13.0% $H_2O$ | 0.35 | 1.44 | .23 | 0.62 |
| at 20.0% $H_2O$ | 0.20 | 1.14 | .16 | .34 |

[a]Reactions were run in a glass reactor containing 2.01 mmole cobalt(II) acetate tetrahydrate, 2.01 mmole manganese(II) acetate tetrahydrate, 4.00 mmole sodium bromide, and 100.0 ml acetic acid. The source of oxygen was air which was passed through a glass frit at the bottom of the reactor at a rate of 52 ml/min. The vent oxygen concentration was constantly measured using a Beckman oxygen analyzer. The rate of oxygen uptake was calculated from the vent oxygen concentration and the flow rate of air through the reactor. The temperature was maintained at 95° C. and the pressure was atmospheric. Examples 17, 18 contained 15.0 ml p-xylene. Examples 19, 20 contained 15.0 ml m-xylene.

Table III presents data using the temperatures and pressures described earlier and these conditions closely represent commercial conditions. The previously discussed data in Tables I and II were generated via low temperature mini-reactor reactions and are used for screening and isolating effects of individual catalyst components.

In example 19 of Table III 225 g of pseudocumene, 420 g of 95% acetic acid, 1.89 g cobalt acetate, 0.84 manganese acetate, 0.053 g of an aqueous solution of zirconium (17 wt%), and 0.34 g of a 48% solution of HBr were charged to a 2-liter autoclave. The temperature of the autoclave was increased to 160° C. and air was introduced to the reactor while stirring. The oxidation initiated at this point and the temperature was increased up to 210° C. and the pressure was increased from 150 psig to 400 psig over a 60-minute period. The pressure helped to control the temperature but the temperature was also controlled by feeding coolant to coils which were submerged in the reactor.

The reactor vent gases were cooled to remove the condensible vapors and the resulting gases were sent to oxygen and $CO_2$ analyzers to measure the extent of reaction and degree of burning. A tail-out catalyst was added continuously to the entire batch cycle. In this example 1.05 g of HBr solution, 0.11 g manganese acetate, and 0.077 g of zirconium solution in 38 g of acetic acid (85% in water) was added to the reactor as the tail-out catalyst. After the vent oxygen level reached 14%, the oxidation was terminated and the reactor contents were collected. A reactor wash was performed and the wash fluid was combined with the reactor effluent and dried. The resulting solids were analyzed for trimellitic acid and by-products. A mole% yield was calculated for each component and the results were normalized to 100% (see Table III).

In example 20 in Table III the procedure was the same but the catalyst concentrations were the following: Initial-4.75 g nickel acetate, 2.00 g manganese acetate, 0.16 g zirconium solution, 0.84 g Hbr solution. Tail-out-2.60 g HBr solution, 0.03 g zirconium solution, 0.55 g manganese acetate.

TABLE III

Comparison of Best Nickel-based Oxidations
with Best Co-based Oxidations of Pseudocumene

| | Example 19 Optimum[1] Cobalt-Based | Example 20 Best[2] Nickel-Based |
|---|---|---|
| TMLA | 89.8 | 89.6 |
| Intermediates | 0.8 | 1.1 |
| Low Boilers | 2.7 | 2.7 |
| High Boilers | 1.2 | 1.1 |
| $CO_x$ | 5.5 | 5.5 |
| Run Time, min. | 65 | 63 |

[1]Cobalt = 0.199 wt %; Initial Mn = 0.084 wt %; Initial Zr = 0.004 wt %; Tail-out Mn = 0.01 wt %; Tail-out Zr = 0.005 wt %; all based on pseudocumene.
[2]Nickel = 0.50 wt %; Initial Mn = 0.20 wt %; Initial Zr = 0.012 wt %; Tail-out Mn = 0.05 wt %; Tail-out Zr = 0.002 wt %; all based on pseudocumene.
Yields were normalized to 100%. Both examples had mass accountabilities of 90.5–91.0.

We claim:

1. A process of oxidizing di- and trimethylbenzenes with molecular oxygen to benzene di- and tricarboxylic acids under liquid-phase conditions in the presence of an aliphatic acid having less than five carbon atoms or in the presence of water or in the presence of a mixture of the aliphatic acid and water at a temperature of about 100° C. to 260° C. and at a pressure to maintain as liquid phase 70–80% of the reaction medium, which process comprises conducting said oxidation in the presence of a catalyst system comprising a source of bromine with nickel, zirconium and manganese wherein for each gram mole of p-xylene, m-xylene, or pseudocumene in the oxidation there is from about 4 to about 20 milligram atom nickel, about 0.10 to about 0.30 milligram atom zirconium, about 2 to about 10 milligram atom total of manganese and from about 8 to 24 milligram atoms bromine.

2. The process of claim 1 wherein the gram atom ratio of nickel:zirconium:manganese is in the range of about 33:1:12 to about 80:1:43 and wherein the solvent is acetic acid or water.

3. The process of claim 2 wherein p-xylene is oxidized to terephthalic acid.

4. The process of claim 2 wherein m-xylene is oxidized to isophthalic acid.

5. The process of claim 2 wherein pseudocumene is oxidized to trimellitic acid.

6. A process for liquid-phase oxidation of a pseudocumene with molecular oxygen under liquid-phase conditions at temperatures in the range of about 100° C. to about 260° C. and at a pressure to maintain as liquid phase 70–80% of the reaction medium, in the presence of a catalyst system comprising a source of bromine with nickel, zirconium and manganese wherein for each gram mole of pseudocumene in the oxidation there is from about 4 to about 20 milligram atom nickel, about 0.10 to about 0.30 milligram atom zirconium, about 2 to about 10 milligram atom total of manganese and from about 8 to 24 milligram atoms bromine.

* * * * *

UNITED STATES PATENT AND TRADEMARK OFFICE
CERTIFICATE OF CORRECTION

PATENT NO. : 4,786,753
DATED : November 22, 1988
INVENTOR(S) : Walter Partenheimer et al It is certified that error appears in the above-identified patent and that said Letters Patent is hereby corrected as shown below:

Column 2, line 4, "nickel-zirconium-manganese" should read --nickel:zirconium:manganese--.

Column 3, line 45, "yield" should read --yields--.

Signed and Sealed this

Fourth Day of July, 1989

Attest:

DONALD J. QUIGG

*Attesting Officer*     *Commissioner of Patents and Trademarks*